(12) United States Patent
Dufort

(10) Patent No.: US 10,878,570 B2
(45) Date of Patent: Dec. 29, 2020

(54) KNOCKOUT AUTOENCODER FOR DETECTING ANOMALIES IN BIOMEDICAL IMAGES

(71) Applicant: International Business Machines Corporation, Armonk, NY (US)

(72) Inventor: Paul Dufort, Toronto (CA)

(73) Assignee: International Business Machines Corporation, Armonk, NY (US)

( * ) Notice: Subject to any disclaimer, the term of this patent is extended or adjusted under 35 U.S.C. 154(b) by 240 days.

(21) Appl. No.: 16/037,264

(22) Filed: Jul. 17, 2018

(65) Prior Publication Data
US 2020/0027211 A1   Jan. 23, 2020

(51) Int. Cl.
*G06T 7/00* (2017.01)
*G06N 3/08* (2006.01)
(Continued)

(52) U.S. Cl.
CPC .......... *G06T 7/0014* (2013.01); *G06K 9/6256* (2013.01); *G06N 3/08* (2013.01);
(Continued)

(58) Field of Classification Search
CPC ................. G06T 7/0012; G06T 7/0014; G06T 2207/20081; G06T 7/13;
(Continued)

(56) References Cited

U.S. PATENT DOCUMENTS 5,331,550 A * 7/1994 Stafford ............... G06K 9/3233
382/128
6,285,992 B1 * 9/2001 Kwasny ............... G06K 9/6267
706/20

(Continued)

FOREIGN PATENT DOCUMENTS

CN       108230257 A     6/2018
WO   WO2017/023569 A1   2/2017

OTHER PUBLICATIONS

High, Rob, "The Era of Cognitive Systems: An Inside Look at IBM Watson and How it Works", IBM Corporation, Redbooks, Dec. 12, 2012, 16 pages.

(Continued)

*Primary Examiner* — Vu Le
(74) *Attorney, Agent, or Firm* — Stephen R. Tkacs; Stephen J. Walder, Jr.; William J. Stock

(57) ABSTRACT

A mechanism is provided in a data processing system comprising a processor and a memory, the memory comprising instructions that are executed by the processor to specifically configure the processor to implement a knockout autoencoder engine for detecting anomalies in biomedical images. The mechanism trains a neural network to be used as a knockout autoencoder that predicts an original based on an input image. The knockout autoencoder engine provides a biomedical image as the input image to the neural network. The neural network outputs a probability distribution for each pixel in the biomedical image. Each probability distribution represents a predicted probability distribution of expected pixel values for a given pixel in the biomedical image. An anomaly detection component executing within the knockout autoencoder engine determines a probability that each pixel has an expected value based on the probability distributions to form a plurality of expected pixel probabilities. The anomaly detection component detects an anomaly in the biomedical image based on the plurality of expected pixel probabilities. An anomaly marking component executing within the knockout autoencoder engine marks the detected anomaly in the biomedical image to form a marked biomedical image and outputs the marked biomedical image.

20 Claims, 7 Drawing Sheets

(51) Int. Cl.
*G06N 7/00* (2006.01)
*G16H 30/40* (2018.01)
*G06T 7/11* (2017.01)
*G06K 9/62* (2006.01)
*G06T 7/143* (2017.01)

(52) U.S. Cl.
CPC .............. *G06N 7/005* (2013.01); *G06T 7/11* (2017.01); *G06T 7/143* (2017.01); *G16H 30/40* (2018.01); *G06K 2209/05* (2013.01); *G06T 2207/20076* (2013.01); *G06T 2207/20081* (2013.01); *G06T 2207/20084* (2013.01); *G06T 2207/30096* (2013.01)

(58) Field of Classification Search
CPC .......... G06T 2207/20076; G06T 7/143; G06T 2207/10081; G06T 2210/41; G01R 33/4808; A61B 5/4064; A61B 5/7267; A61B 5/1032; A61B 5/7485; A61B 8/08; A61B 5/444; A61B 5/68; G01N 2469/20; G01N 3/08; G02B 21/367; G06K 9/6256; G06K 9/6292; G06K 2009/00738; G06K 9/00771; G06K 9/00127; G06K 9/6212; G06K 9/6217; G06K 9/628; G06K 9/00885; G06K 9/6267; G16H 30/20; G16H 30/40; G16H 50/20; G16H 50/70; G16H 50/50; G06N 3/08; G06N 7/005; G06N 20/00; G06N 3/02; B60R 21/01538; G01S 15/06; G01S 7/417; G06F 19/00
USPC ....... 382/128, 131, 156, 132, 129, 130, 199, 382/173, 159, 224; 345/418
See application file for complete search history.

(56) References Cited

U.S. PATENT DOCUMENTS

| | | | | |
|---|---|---|---|---|
| 7,260,250 B2* | 8/2007 | Summers | ............... | G16H 15/00 382/128 |
| 8,041,651 B2* | 10/2011 | Greer | ..................... | G06N 3/04 706/12 |
| 10,074,038 B2* | 9/2018 | Hsieh | ..................... | G06K 9/036 |
| 10,127,659 B2* | 11/2018 | Hsieh | ..................... | G06F 19/00 |
| 10,223,590 B2* | 3/2019 | Chen | ..................... | G06T 7/194 |
| 10,402,700 B2* | 9/2019 | van den Oord | .......... | G06K 9/66 |
| 10,417,788 B2* | 9/2019 | Risman | ................... | G06T 9/002 |
| 2003/0194124 A1 | 10/2003 | Suzuki et al. | | |
| 2004/0109608 A1* | 6/2004 | Love | ..................... | G06K 9/46 382/224 |
| 2004/0161138 A1* | 8/2004 | Ashton | ..................... | G06T 7/11 382/128 |
| 2006/0018524 A1 | 1/2006 | Suzuki et al. | | |
| 2015/0003699 A1* | 1/2015 | Davis | ................... | A61B 5/6898 382/128 |
| 2016/0035093 A1 | 2/2016 | Kateb et al. | | |
| 2017/0109881 A1* | 4/2017 | Avendi | ..................... | G06T 7/149 |
| 2017/0148166 A1 | 5/2017 | Alpert et al. | | |
| 2017/0236292 A1* | 8/2017 | Lin | ..................... | G06K 9/4628 382/173 |
| 2017/0371017 A1 | 12/2017 | Odry et al. | | |
| 2018/0033144 A1* | 2/2018 | Risman | ................... | G16H 30/20 |
| 2018/0165554 A1* | 6/2018 | Zhang | ................... | G06K 9/6256 |
| 2018/0285695 A1* | 10/2018 | Guo | ................... | G06T 7/0012 |
| 2018/0330518 A1* | 11/2018 | Choi | ................... | A61B 8/5223 |

OTHER PUBLICATIONS

Ronneberger, Olaf et al., "U-Net: Convolutional Networks for Biomedical", arXiv: 1505.04597v1 [cs.CV], May 18, 2015, 8 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

International Search Report and Written Opinion dated Oct. 28, 2019 for International Application No. PCT/IB2019/056008, 9 pages.

* cited by examiner

*FIG. 4*
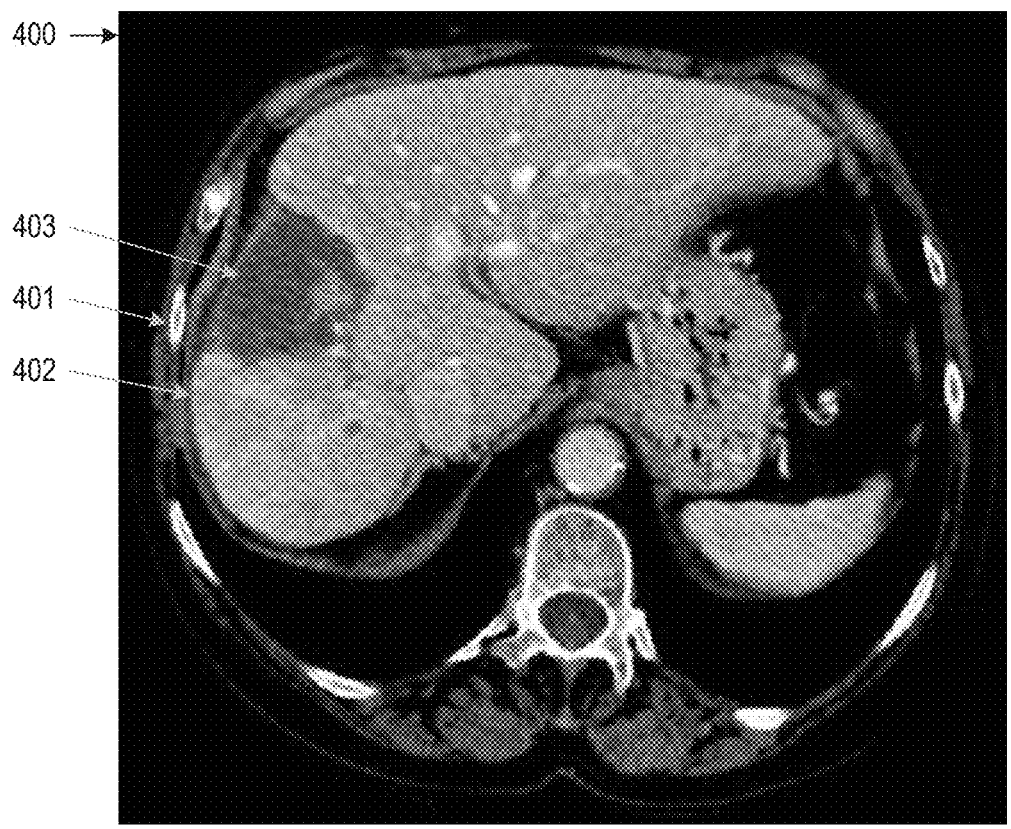
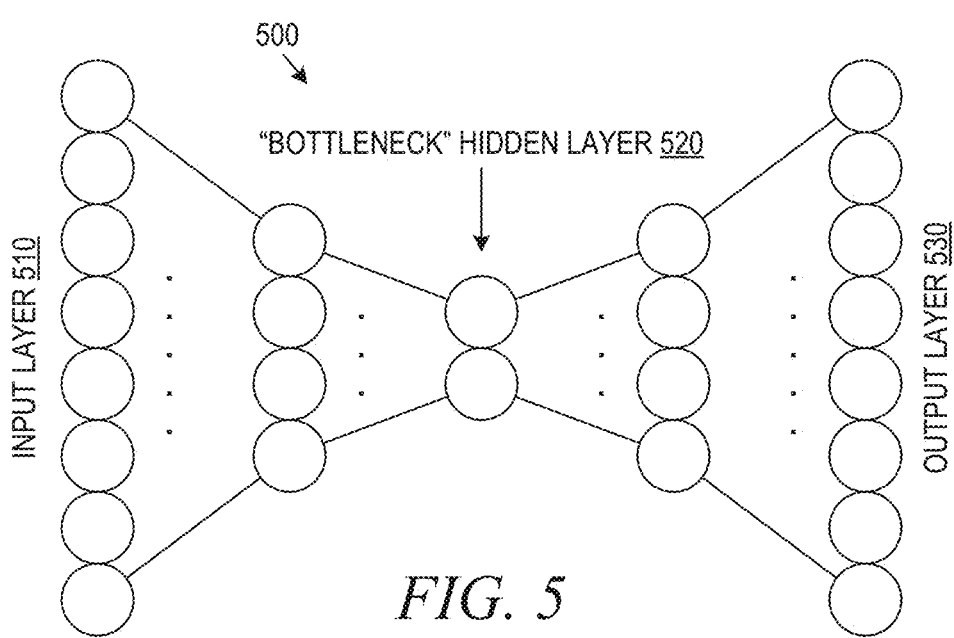
*FIG. 5*

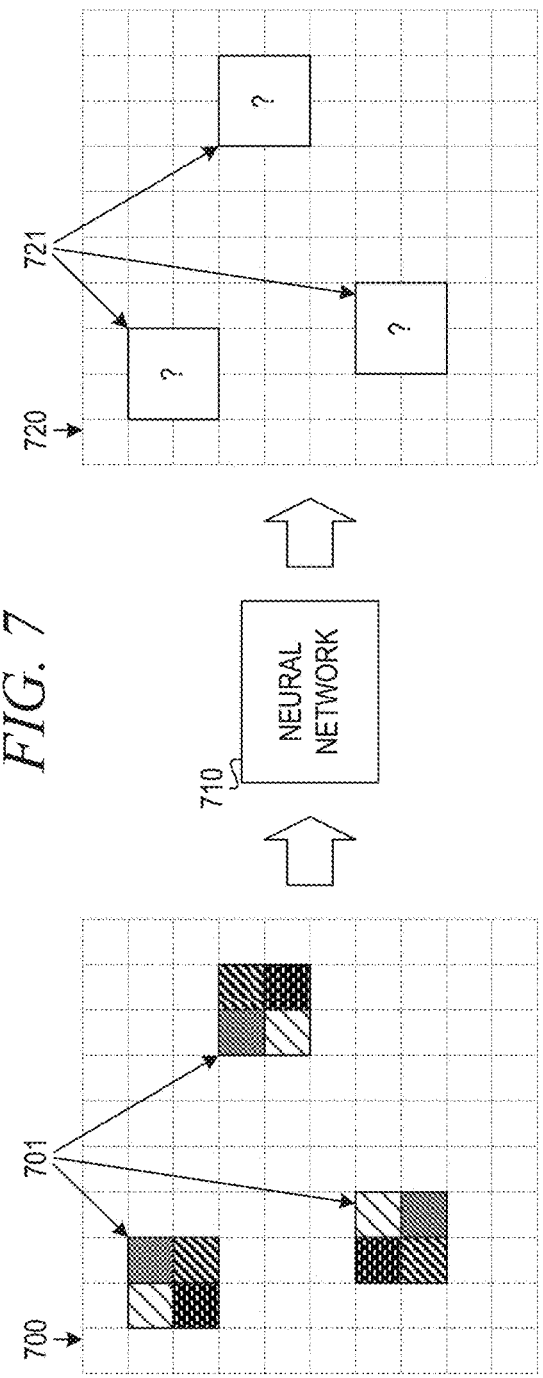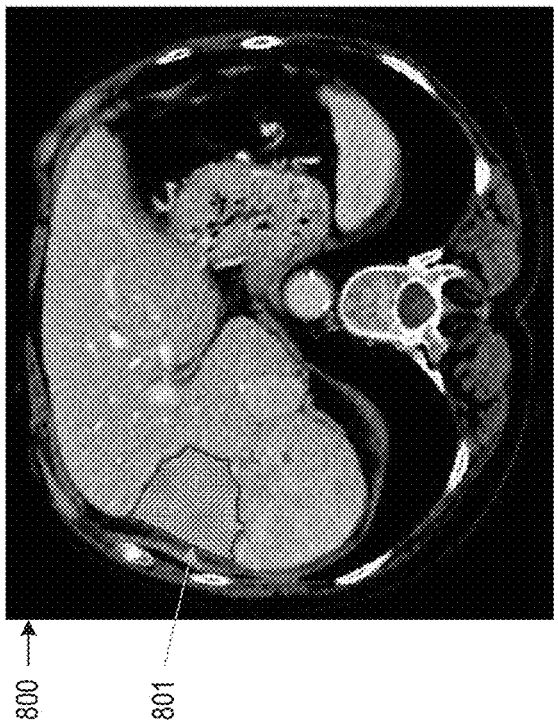
FIG. 7
FIG. 8

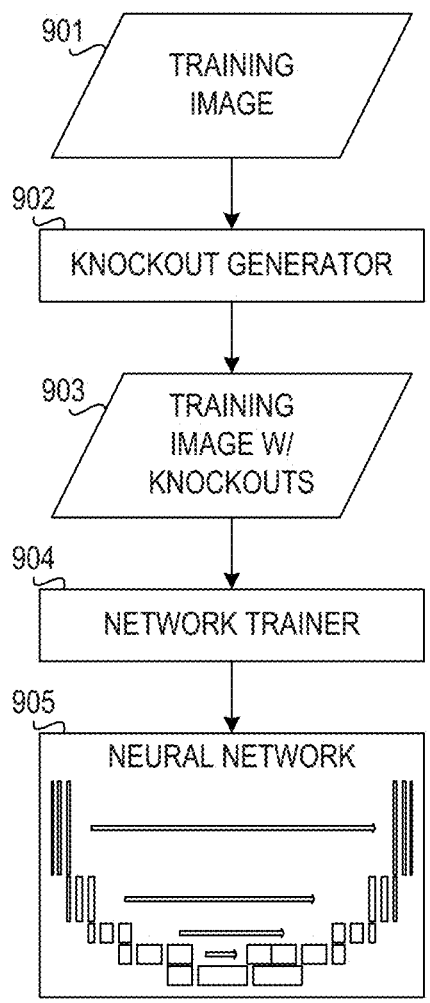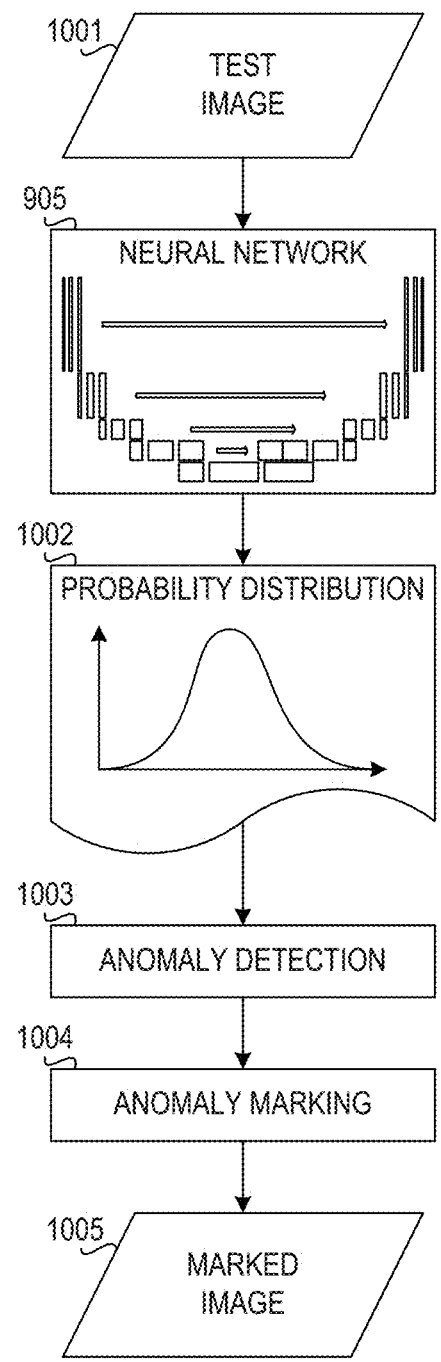

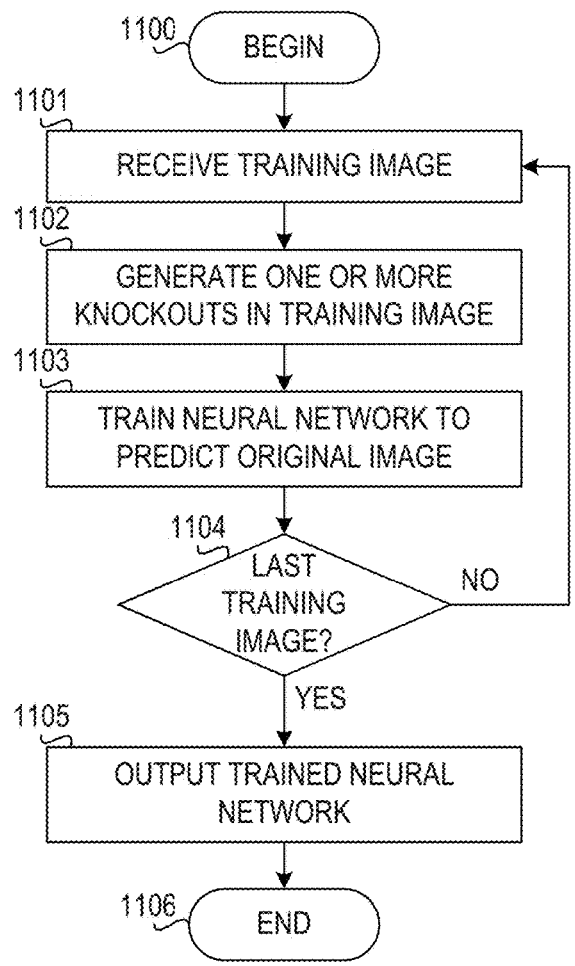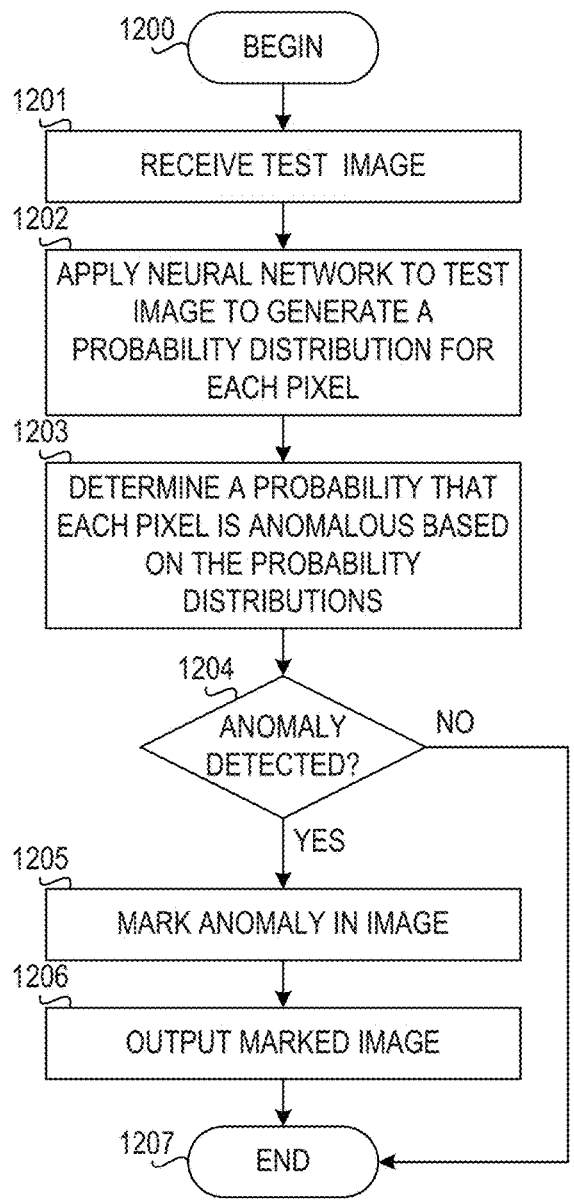

KNOCKOUT AUTOENCODER FOR DETECTING ANOMALIES IN BIOMEDICAL IMAGES

BACKGROUND

The present application relates generally to an improved data processing apparatus and method and more specifically to mechanisms for training and using a knockout autoencoder for detecting anomalies in biomedical images.

In machine learning, a convolutional neural network (CNN, or ConvNet) is a class of deep, feed-forward artificial neural networks, most commonly applied to analyzing visual imagery. CNNs use a variation of multilayer perceptrons designed to require minimal preprocessing. CNNs are also known as shift invariant or space invariant artificial neural networks (SIANN), based on their shared-weights architecture and translation invariance characteristics. Convolutional networks were inspired by biological processes in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field. CNNs use relatively little pre-processing compared to other image classification algorithms. This means that the network learns the filters that in traditional algorithms were hand-engineered. This independence from prior knowledge and human effort in feature design is a major advantage. They have applications in image and video recognition, recommender systems and natural language processing.

The U-Net is a convolutional neural network that was developed for biomedical image segmentation. The network is based on the fully convolutional network and its architecture was modified and extended to work with fewer training images and to yield more precise segmentations. The network consists of a contracting path and an expansive path, which gives it the u-shaped architecture. The contracting path is a typical convolutional network that consists of repeated application of convolutions, each followed by a rectified linear unit (ReLU) and a max pooling operation. During the contraction, the spatial information is reduced while feature information is increased. The expansive pathway combines the feature and spatial information through a sequence of up-convolutions and concatenations with high-resolution features from the contracting path.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory, the memory comprising instructions that are executed by the processor to specifically configure the processor to implement a knockout autoencoder engine for detecting anomalies in biomedical images. The method comprises training a neural network to be used as a knockout autoencoder that predicts an original based on an input image. The method further comprises providing, by the knockout autoencoder engine, a biomedical image as the input image to the neural network. The method further comprises outputting, by the neural network, a probability distribution for each pixel in the biomedical image. Each probability distribution represents a predicted probability distribution of expected pixel values for a given pixel in the biomedical image. The method further comprises determining, by an anomaly detection component executing within the knockout autoencoder engine, a probability that each pixel has an expected value based on the probability distributions to form a plurality of expected pixel probabilities. The method further comprises detecting, by the anomaly detection component, an anomaly in the biomedical image based on the plurality of expected pixel probabilities. The method further comprises marking, by an anomaly marking component executing within the knockout autoencoder engine, the detected anomaly in the biomedical image to form a marked biomedical image. The method further comprises outputting, by the knockout autoencoder engine, the marked biomedical image.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 4 depicts an example biomedical image with an anomaly which may be detected by the knockout encoder of the illustrative embodiments;

FIG. 5 depicts an example neural network autoencoder in accordance with an illustrative embodiment;

FIG. 7 illustrates use of a neural network for a knockout autoencoder in accordance with an illustrative embodiment;

FIG. 8 illustrates an output image marked with a detected abnormality in accordance with an illustrative embodiment;

FIG. 9 is a block diagram of a mechanism for training a neural network to be used as a knockout autoencoder for detecting anomalies in biomedical images in accordance with an illustrative embodiment;

FIG. 10 is a block diagram of a mechanism for using a knockout autoencoder to detect anomalies in biomedical images in accordance with an illustrative embodiment;

FIG. 11 is a flowchart illustrating operation of a mechanism for training a neural network to be used as a knockout autoencoder for detecting anomalies in biomedical images in accordance with an illustrative embodiment; and FIG. 12 is a flowchart illustrating operation of a mechanism for using a knockout autoencoder to detect anomalies in biomedical images in accordance with an illustrative embodiment.

DETAILED DESCRIPTION

Figure 1:
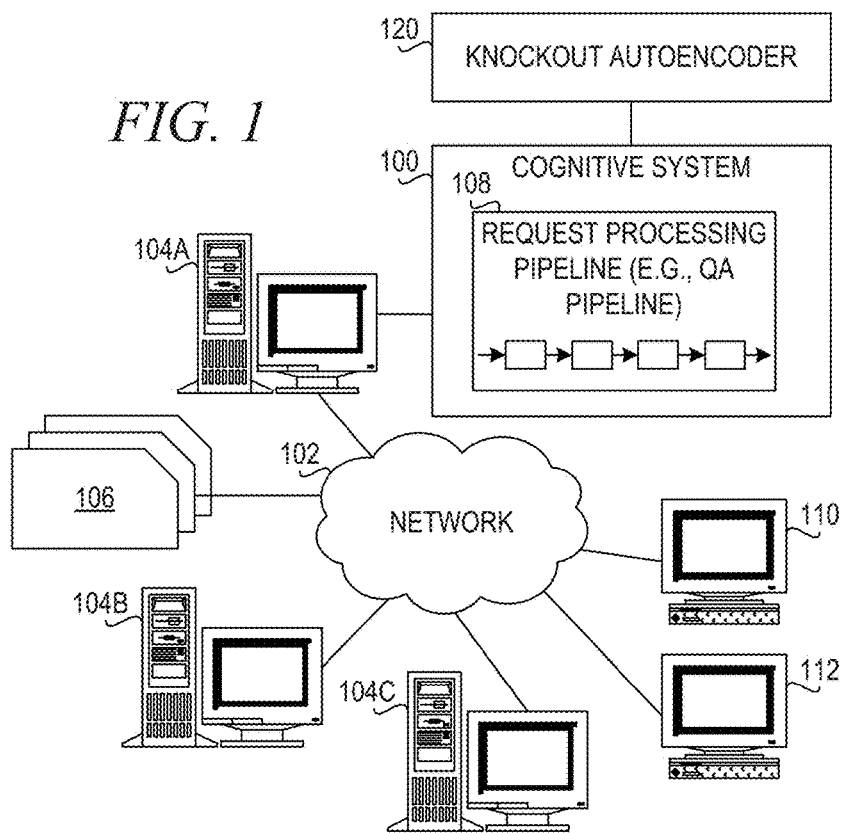
FIG. 1 depicts a schematic diagram of one illustrative embodiment of a cognitive healthcare system in a computer network.

Convolutional neural networks (CNNs) pick up structures that have regularity. Biomedical image segmentation seeks to focus attention on image pixels that represent an object of interest. Once such objects are identified, systems can calculate volumes or shapes and look for organ-specific findings. CNNs are good at segmentation because they exploit consistent shapes and contexts. However, it is difficult to segment shapes that are not regular (e.g., tumor masses, lesions, etc.). In other words, current mechanisms do not segment well irregular shapes in medical images, i.e., shapes that vary in geometry, intensity, etc.

The illustrative embodiment uses CNNs to detect abnormalities by detecting the absence of a regularity that these abnormalities obscure. The illustrative embodiments provide a mechanism for using the rest of a medical image to predict what should be at a particular location in the medical image. Based on this prediction, the mechanism may use discrepancies from the prediction to determine when something is highly unexpected in that location. That is, the mechanism of the illustrative embodiment detects abnormalities by determining if a medical image does not have what would have been expected.

The mechanism of the illustrative embodiment takes an input, passes it through a neural network, and attempts to reconstruct the input layer at the output layer. While this may seem straightforward, the key is that the mechanism makes the task difficult in a way that works to an advantage.

In a classic autoencoder, the difficulty would be achieved by limiting the degrees of freedom so that the network learns to represent the input with far fewer variables, i.e., dimensionality reduction. The illustrative embodiment, however, repurposes a U-net as the autoencoder and introduces "knockouts," which are random patches in the image that are filled with noise. The U-net is then trained to predict the original image contents (before noise) using only the rest of the image, i.e., the portion of the image that does not include the knockouts. Thus, the U-net learns how to recreate the original image by computing the distribution of values in the knockout area that it predicts should be there based on other values in the image. The network will highlight with low probability the portions of an image that are abnormal.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network anchor a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
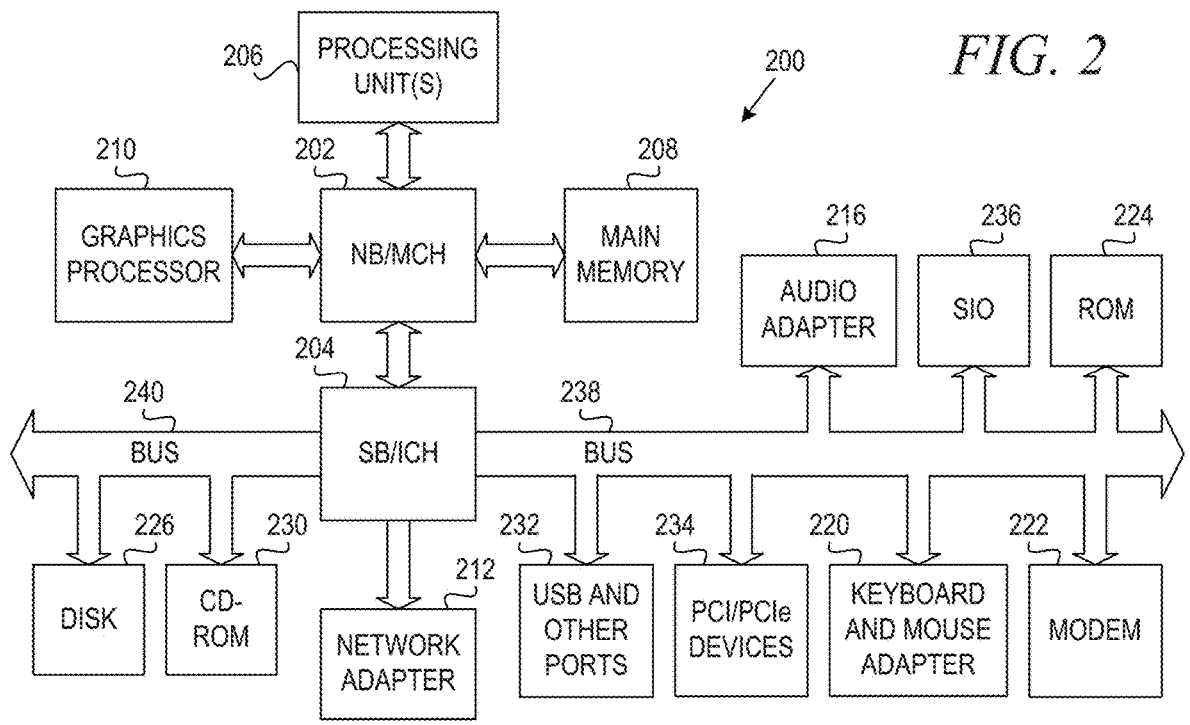
FIG. 2 is a block diagram of an example data processing system in which aspects of the illustrative embodiments are implemented.
Figure 3:
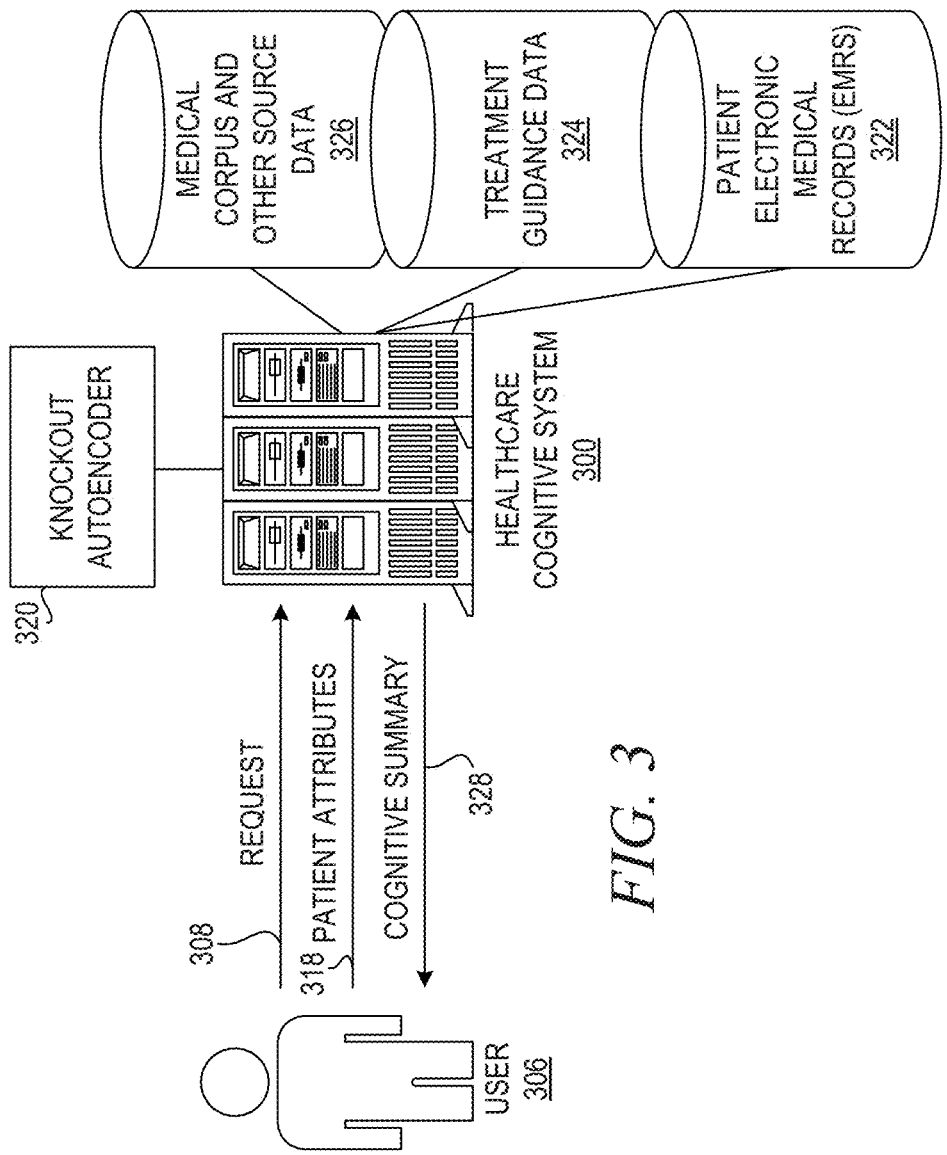
FIG. 3 is an example diagram illustrating an interaction of elements of a healthcare cognitive system in accordance with one illustrative embodiment.

As noted above, the present invention provides mechanisms for detecting anomalies in biomedical images. The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for presenting relevant information using a graphical presentation engine.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for cognitive analysis of EMR data, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. These corpora may include, but are not limited to, EMR data. The cognitive system may use a knockout autoencoder for detecting anomalies in biomedical images.

As will be discussed in greater detail hereafter, the illustrative embodiments may be integrated in, augment, and extend the functionality of these QA pipeline, or request processing pipeline, mechanisms of a healthcare cognitive system with regard to an electronic medical record completeness and data quality assessment mechanism. Thus, it is important to first have an understanding of how cognitive systems and question and answer creation in a cognitive system implementing a QA pipeline is implemented before describing how the mechanisms of the illustrative embodiments are integrated in and augment such cognitive systems and request processing pipeline, or QA pipeline, mechanisms. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

FIG. 1 depicts a schematic diagram of one illustrative embodiment of a cognitive system 100 implementing a request processing pipeline 108 in a computer network 102. The cognitive system 100 is implemented on one or more computing devices 104A-C (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-C. The network 102 includes multiple computing devices 104A-C, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 may provide cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. The requests may be posed in the form of a natural language question, natural language request for information, natural language request for the performance of a cognitive operation, or the like, and the answer may be returned in a natural language format maximized for efficient comprehension in a point-of-care clinical setting. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-C on the network 102 include access points for content creators and cognitive system users. Some of the computing devices 104A-C include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions/requests to the cognitive system 100 that are answered/processed based on the content in the corpus or corpora of data 106. In one embodiment, the questions/requests are formed using natural language. The cognitive system 100 parses and interprets the question/request via a pipeline 108, and provides a response to the cognitive system user, e.g., cognitive system user 110, containing one or more answers to the question posed, response to the request, results of processing the request, or the like. In some embodiments, the cognitive system 100 provides a response to users in a ranked list of candidate answers/responses while in other illustrative embodiments, the cognitive system 100 provides a single final answer/response or a combination of a final answer/response and ranked listing of other candidate answers/responses.

The cognitive system 100 implements the pipeline 108, which comprises a plurality of stages for processing an input question/request based on information obtained from the corpus or corpora of data 106. The pipeline 108 generates answers/responses for the input question or request based on the processing of the input question/request and the corpus or corpora of data 106.

In some illustrative embodiments, the cognitive system 100 may be the IBM Watson™ cognitive system available from International Business Machines Corporation of Armonk, New York, which is augmented with the mechanisms of the illustrative embodiments described hereafter. As outlined previously, a pipeline of the IBM Watson™ cognitive system receives an input question or request which it then parses to extract the major features of the question/request, which in turn are then used to formulate queries that are applied to the corpus or corpora of data 106. Based on the application of the queries to the corpus or corpora of data 106, a set of hypotheses, or candidate answers/responses to the input question/request, are generated by looking across the corpus or corpora of data 106 for portions of the corpus or corpora of data 106 (hereafter referred to simply as the corpus 106) that have some potential for containing a valuable response to the input question/response (hereafter assumed to be an input question). The pipeline 108 of the IBM Watson™ cognitive system then performs deep analysis on the language of the input question and the language used in each of the portions of the corpus 106 found during the application of the queries using a variety of reasoning algorithms.

The scores obtained from the various reasoning algorithms are then weighted against a statistical model that summarizes a level of confidence that the pipeline 108 of the IBM Watson™ cognitive system 100, in this example, has regarding the evidence that the potential candidate answer is inferred by the question. This process may be repeated for each of the candidate responses to generate a ranked listing of candidate responses, which may then be presented to the user that submitted the input request, e.g., a user of client computing device 110, or from which a final response is selected and presented to the user. More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An inside Look at IBM Watson and How it Works" by Rob High, IBM Redbooks, 2012.

As noted above, while the input to the cognitive system 100 from a client device may be posed in the form of a natural language request, the illustrative embodiments are not limited to such. Rather, the input request may in fact be formatted or structured as any suitable type of request which may be parsed and analyzed using structured and/or unstructured input analysis, including but not limited to the natural language parsing and analysis mechanisms of a cognitive system such as IBM Watson™, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a knockout autoencoder engine 120 for using a convolutional neural network (CNN) to predict each pixel or voxel of an input biomedical image based on the rest of the input biomedical image. The knockout autoencoder engine 120 then detects anomalies by determining if the biomedical image does not have in it what is expected.

Knockout autoencoder engine 120 is provided with a CNN that is repurposed and trained as an autoencoder to predict the original image. In one embodiment, the CNN is a U-net that is trained by providing training images with "knockouts" that are random patches in the image that are lifted with noise. The U-net is trained to predict the original image contents before the noise were introduced using only the rest of the image. Thus, the U-net learns how to recreate the original image by computing the distribution values in the knockout area that it predicts should be there based on the other values in the image.

Given a test image, knockout autoencoder engine 120 generates for each pixel a probability distribution of values. Knockout autoencoder engine 120 uses each probability distribution value to determine whether the pixel in question is what is expected based on the other pixels in the image. Knockout autoencoder engine 120 may also mark detected anomalies in the image and output the marked image to user. As used herein, a test image may be an image that is used to test the accuracy of the knockout autoencoder engine 120 or an image for which a user wishes to detect abnormalities or anomalies.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements a cognitive system 100 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as bound in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a cognitive summary of EMR data for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the user 306 as a human figure, the interactions with user 306 may be performed using computing devices, medical equipment, and/or the like, such that user 306 may in fact be a computing device, e.g., a client computing device. For example, interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, the user 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302, social history, and demographic information about the patient, symptoms, and other pertinent information obtained from responses to questions or information obtained from medical equipment used to monitor or gather data about the condition of the patient. In one embodiment, patient attributes 318 may include identification of a biomedical image for processing to detect anomalies. Any information about the patient that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a cognitive summary of EMR data 328 to the user 306 to assist the user 306 in treating the patient based on their reported symptoms and other information gathered about the patient. The healthcare cognitive system 300 operates on the request 308 and patient attributes 318 utilizing information gathered from the medical corpus and other source data 326, treatment guidance data 324, and the patient EMRs 322 associated with the patient to generate cognitive summary 328. In one embodiment, patient EMR data 322 may include biomedical images. The cognitive summary 328 may be presented in a ranked ordering with associated supporting evidence, obtained from the patient attributes 318 and data sources 322-326, indicating the reasoning as to why portions of EMR data 322 are being provided. Cognitive summary 328 may also include a marked image that identifies detected anomalies.

In accordance with the illustrative embodiments herein, the healthcare cognitive system 300 is augmented to include a knockout autoencoder engine 320 for using a convolutional neural network (CNN) to predict each pixel or voxel of an input biomedical image based on the rest of the input biomedical image. The knockout autoencoder engine 320 then detects anomalies by determining if the biomedical image does not have in it what is expected.

FIG. 4 depicts an example biomedical image with an anomaly which may be detected by the knockout encoder of the illustrative embodiments. A convolutional neural network (CNN) for segmentation is trained to detect expected structures, such as a rib 401. A CNN, such as a U-net, learns that a structure such as a rib 401 will often be adjacent to a structure such as a liver 402, or vice versa. That is, the CNN is trained to learn where to expect certain structures in a biomedical image based on a set of training images.

An anomaly or abnormality, such as lesion 403, obscures areas where such a structure is to be expected. Lesions have very little regularity, because they have highly variable locations, sizes, shapes, intensity patterns, etc. CNNs achieve better performance at lesion segmentation not by detecting their regularity but by detecting the absence of the regularity that they obscure.

The illustrative embodiments attempt to identify anomalies by arguing that what is there is not what is expected to be found there. Specifically, the illustrative embodiments can get the rest of the image to predict what should be at a particular location and detect when something highly unexpected is at that location.

FIG. 5 depicts an example neural network autoencoder in accordance with an illustrative embodiment. The purpose of autoencoder is to take the input at input layer 510, pass it through the network 500, and recreate the input at output layer 530. The key is to make it difficult in a way that works to the advantage of the autoencoder. In the classical autoencoder, this is done by limiting the degrees of freedom, so that the network learns to represent the input with far fewer variables, i.e., dimensionality reduction. This difficulty is manifested as a "bottleneck" in hidden layer 520.

Figure 6:
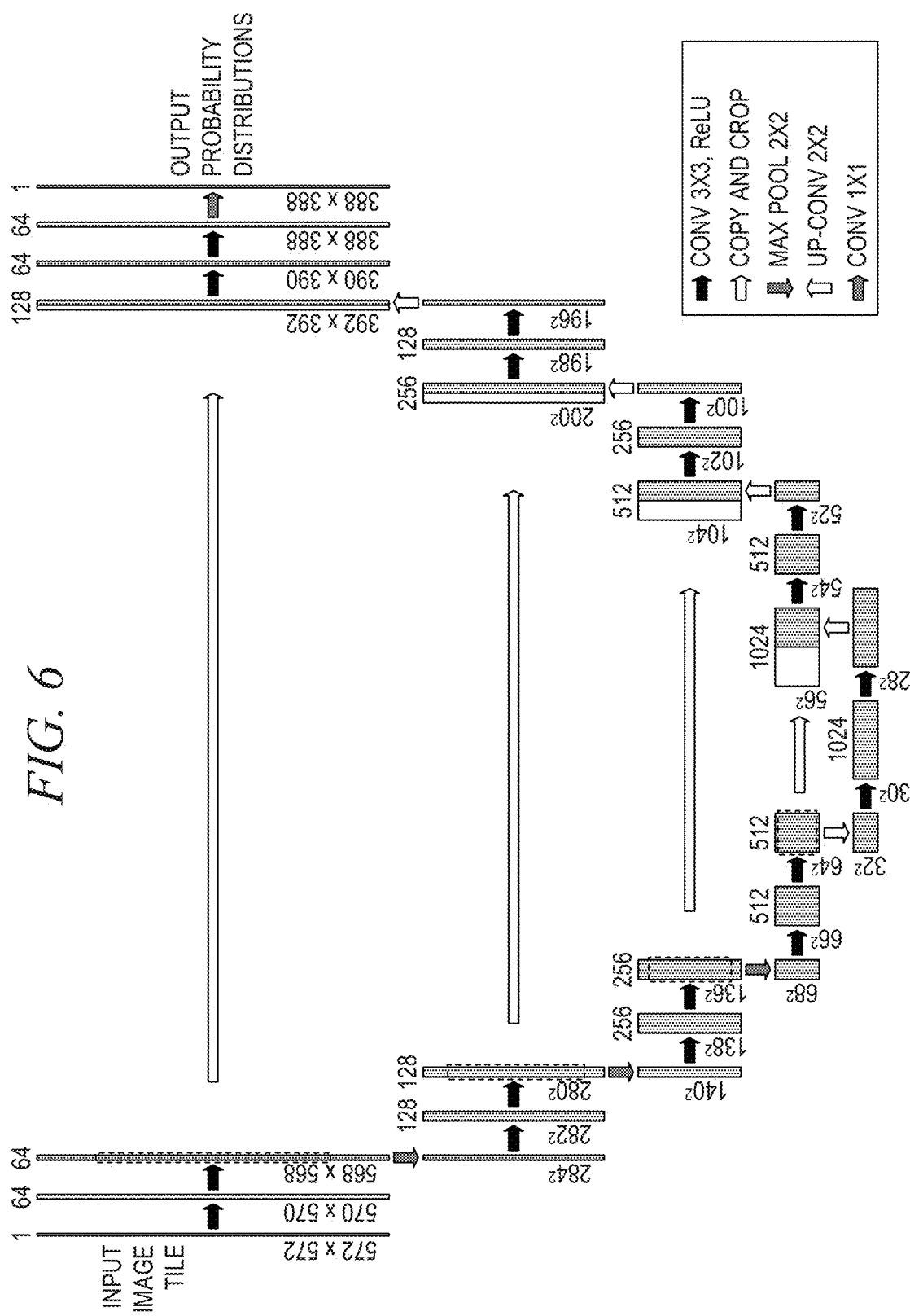
FIG. 6 depicts a U-net that is repurposed as an autoencoder in accordance with an illustrative embodiment.

FIG. 6 depicts a U-net that is repurposed as an autoencoder in accordance with an illustrative embodiment. The U-net is currently the best performing network for semantic segmentation. The U-net architecture shown in FIG. 6 is an example for 32×32 pixels in the lowest resolution. The U-net architecture consists of a contracting path (left side) and an expansive path (right side). The contracting path follows the typical architecture of a convolutional network. It consists of the repeated application of two 3×3 convolutions (unpadded convolutions). Each shaded box corresponds to a multi-channel feature map. The number of channels is denoted on the top of each box. The x-y size is provided at the lower left edge of the box. White boxes represent copied feature maps. The arrows denote the different operations. The horizontal black arrows represent 3×3 convolutions (unpadded convolutions), each followed by a rectified linear unit (ReLU) and a 2×2 max pooling operation with stride 2 for down-sampling, represented by the vertical shaded arrows. At each down-sampling step, the number of feature channels is doubled. Every step in the expansive path consists of an up-sampling of the feature map followed by a 2×2 convolution ("up-convolution"), represented by the vertical white arrows, that halves the number of feature channels, a concatenation with the correspondingly cropped feature map from the contracting path, represented by the horizontal white arrows, and two 3×3 convolutions, each followed by a ReLU. The cropping is necessary due to the loss of border pixels in every convolution. At the final layer, a 1×1 convolution, represented by the shaded horizontal arrow, is used to map each 64-component feature vector to the desired number of classes. In total, the network has 23 convolutional layers.

The U-net architecture shown in FIG. 6 is an example CNN that is known for biomedical image segmentation; however, the illustrative embodiments modify and repurpose the U-net architecture to train the U-net as an autoencoder. The illustrative embodiments introduce a way of making the problem difficult that works to the advantage of the autoencoder. FIG. 7 illustrates use of a neural network for a knockout autoencoder in accordance with an illustrative embodiment. The illustrative embodiments choose random patches 701 in the input image tile 700 and fill them with noise. The illustrative embodiments then train the neural network 710 to predict the original image contents, before introduction of noise, using only the rest of the image. Thus, the U-net is trained to generate for each pixel an output probability distribution for predicting pixel values that are expected in the original image. The probability distribution may be a parametric distribution, such as a bell curve, Gaussian distribution, etc., with the peak at the most probable value. The illustrative embodiments use the output probability distributions to determine what is expected to be in knockout patches 721 in the output image 720.

FIG. 8 illustrates an output image marked with a detected abnormality in accordance with an illustrative embodiment. For a test image 800, the illustrative embodiment applies the knockout autoencoder to the test image 800. For each pixel in the image 800, the knockout autoencoder generates a probability distribution that predicts the pixel value that is expected at that location in the image. In one embodiment, the illustrative embodiment determines, for each pixel in the input image, the probability that the input value for that pixel is the expected value according to the probability distribution for that pixel. The illustrative embodiment may then compare that probability to a predetermined threshold. If the probability is above the threshold, then the illustrative embodiment may determine that the pixel value is within an expected range. If the probability for a given pixel is below the predetermined threshold, then the illustrative embodiment may determine that the pixel value is highly unexpected and, thus, may be part of an anomaly or abnormality.

In one embodiment, the illustrative embodiment marks the pixels determined to be an anomaly or abnormality, thus forming a marked anomaly 801. In one embodiment, the pixels to be marked are detected using a threshold as described, and those identified as improbable may have a pixel set to 1 in an overlay image, or zero if they are normal. The overlay is then rendered semi-transparently in color, for example, so that regions marked as abnormal appear red, while the normal regions are fully transparent and only show the original image underneath the overlay.

FIG. 9 is a block diagram of a mechanism for training a neural network to be used as a knockout autoencoder for detecting anomalies in biomedical images in accordance with an illustrative embodiment. A training image 901 is provided to knockout generator component 902, which chooses random patches in the training image 901 and fills the patches with noise to form a training image with knockouts 903. Network trainer 904 then trains neural network 905 to predict the original training image 901 given the training image with knockouts 903. More specifically, network trainer 904 trains neural network 905 to predict each pixel value using the rest of the image 903.

The process of training neural network 905 is repeated for a plurality of training images, which are selected from healthy patients. That is training images 901 are biomedical images having no abnormalities, such as tumors or lesions. That is, the training images 901 are inherently labeled with expected values for supervised learning, because the pixel values can be assumed to be as expected for a healthy patient. Given a variety of training images 901, network trainer 904 is able to train neural network 905 to accurately predict a given pixel value using the remainder of the image. Thus, even for a pixel with random noise in a knockout patch, the neural network 905 is trained to predict the expected value for that pixel, which is known in training image 901, using the rest of the image.

Neural network 905 may be a convolutional neural network. In one embodiment neural network 905 is a U-net, which is known to be used for segmentation, but is repurposed and trained to be an autoencoder.

FIG. 10 is a block diagram of a mechanism for using a knockout autoencoder to detect anomalies in biomedical images in accordance with an illustrative embodiment. A test image 1001 is an image used to test the knockout autoencoder or an image for which a user wishes to detect anomalies. Test image 1001 is provided as input to neural network 905, which generates for each pixel a probability distribution 1002. Each probability distribution represents a prediction of a pixel value for a given pixel of test image 1001 based on the rest of the pixels in the image. The probability distribution 1002 may be a parametric distribution, such as a Gaussian distribution, centered around the pixel having the highest probability.

Anomaly detection component 1003 compares each pixel value in test image 1001 to its corresponding probability distribution 1002. That is, for a given pixel value in image 1001, its probability distribution 1002 gives a probability value indicating the probability that the pixel value is the expected value. Anomaly detection component 1003 may then compare the probability value of each pixel to a predetermined threshold. For pixels in test image 1001 having probability values below the threshold, anomaly detection component 1003 detects that those pixels make up an anomaly. Anomaly marking component 1004 then marks those pixels as part of an anomaly and outputs a marked image 1005.

FIG. 11 is a flowchart illustrating operation of a mechanism for training a neural network to be used as a knockout autoencoder for detecting anomalies in biomedical images in accordance with an illustrative embodiment. Operation begins (block 1100), and the mechanism receives a training image (block 1101). The mechanism generates one or more knockouts in the training image and fills them with noise (block 1102). The mechanism trains the network to predict the original image before the introduction of noise (block 1103).

The mechanism determines whether the image is the last training image (block 1104). If the current image is not the last training image, then operation returns to block 1101 to receive the next training image. If the current image is the last training image at block 1104, then the mechanism outputs the trained neural network (block 1105). The traversal of each training image once is called an epoch. Typically there will be many epochs in a training session, so that each image is seen multiple times. In the current embodiment, however, each time the same image is seen, the random knocked out patches will be different. Thereafter, operation ends (block 1106).

FIG. 12 is a flowchart illustrating operation of a mechanism for using a knockout autoencoder to detect anomalies in biomedical images in accordance with an illustrative embodiment. Operation begins (block 1200), and the mechanism receives a test image (block 1201). A test image may be an unlabeled image for testing the autoencoder or may be a biomedical image for which a user wants to detect anomalies. The mechanism applies the neural network to the test image to generate a probability distribution for each pixel (block 1202). The mechanism then determines a probability that each pixel is part of an anomaly based on the probability distributions (block 1203).

The mechanism determines whether an anomaly is detected (block 1204). For each pixel, the mechanism may compare the probability that the pixel value is what the autoencoder predicted or expected to a predetermined threshold. The mechanism may then determine whether one or more pixels represent an anomaly or abnormality in the test image. The U-net usually does a very good job by itself; however, in cases where the U-net does not do as good a job as desired, in one embodiment the mechanism runs a post-processing step on the output employing a conditional random field model (CRF) to clean up the result by filling holes, removing specks, and smoothing boundaries of detected regions. An even simpler and older method is to just do a connected components analysis and not mark any components (connected regions) that are below a certain threshold size. The U-net works so well that applying these cleanup post-processing steps is likely unnecessary. If an anomaly is detected, the mechanism marks the anomaly in the image (block 1205). Then, the mechanism outputs the marked image (block 1206), and operation ends (block 1207). If an anomaly is not detected in block 1204, then operation ends (block 1207).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory, the memory comprising instructions that are executed by the processor to specifically configure the processor to implement a knockout autoencoder engine for detecting anomalies in biomedical images, the method comprising:

training a neural network to be used as a knockout autoencoder that predicts an original image based on an input image, wherein training the neural network comprises:
for each training image in a set of training images, selecting one or more knockout patches of the training image, filling the one or more knockout patches with noise to form a knockout image, and training the neural network to predict the training image based on expected content in the knockout patches of the knockout image given remaining pixels in the knockout image;

providing, by the knockout autoencoder engine, a biomedical image as the input image to the neural network;

outputting, by the neural network, a probability distribution for each pixel in the biomedical image, wherein each probability distribution represents a predicted probability distribution of expected pixel values for a given pixel in the biomedical image;

determining, by an anomaly detection component executing within the knockout autoencoder engine, a probability that each pixel has an expected value based on the probability distributions to form a plurality of expected pixel probabilities;

detecting, by the anomaly detection component, an anomaly in the biomedical image based on the plurality of expected pixel probabilities;

marking, by an anomaly marking component executing within the knockout autoencoder engine, the detected anomaly in the biomedical image to form a marked biomedical image; and outputting, by the knockout autoencoder engine, the marked biomedical image.

2. The method of claim 1, wherein the set of training images comprise a plurality of biomedical images of healthy patients.

3. The method of claim 1, wherein selecting one or more knockout patches comprises selecting one or more random patches in the training image.

4. The method of claim 1, wherein the neural network comprises a convolutional neural network.

5. The method of claim 4, wherein the convolutional neural network comprises a U-net.

6. The method of claim 1, wherein determining the probability that each pixel has an expected value based on the probability distributions comprises:
for each given pixel in the biomedical image having a given pixel value, identifying a probability value corresponding to the given pixel value in a given probability distribution corresponding to the given pixel.

7. The method of claim 1, wherein detecting the anomaly in the biomedical image based on the plurality of expected pixel probabilities comprises:
comparing each expected pixel probability in the plurality of expected pixel probabilities to a predetermined threshold; and
responsive to one or more of the plurality of expected pixel probabilities being less than the predetermined threshold, determining that the biomedical image has an anomaly.

8. A computer program product comprising a non-transitory computer readable medium having a computer readable program stored therein, wherein the computer readable program, when executed on a computing device, causes the computing device to implement a knockout autoencoder engine for detecting anomalies in biomedical images, wherein the computer readable program causes the computing device to:

train a neural network to be used as a knockout autoencoder that predicts an original image based on an input image, wherein training the neural network comprises:
        for each training image in a set of training images, selecting one or more knockout patches of the training image, filling the one or more knockout patches with noise to form a knockout image, and training the neural network to predict the training image based on expected content in the knockout patches of the knockout image given remaining pixels in the knockout image;

provide, by the knockout autoencoder engine, a biomedical image as the input image to the neural network;

output, by the neural network, a probability distribution for each pixel in the biomedical image, wherein each probability distribution represents a predicted probability distribution of expected pixel values for a given pixel in the biomedical image;

determine, by an anomaly detection component executing within the knockout autoencoder engine, a probability that each pixel has an expected value based on the probability distributions to form a plurality of expected pixel probabilities;

detect, by the anomaly detection component, an anomaly in the biomedical image based on the plurality of expected pixel probabilities;

mark, by an anomaly marking component executing within the knockout autoencoder engine, the detected anomaly in the biomedical image to form a marked biomedical image; and output, by the knockout autoencoder engine, the marked biomedical image.

9. The computer program product of claim 8, wherein set of training images comprise a plurality of biomedical images of healthy patients.

10. The computer program product of claim 8, wherein selecting one or more knockout patches comprises selecting one or more random patches in the training image.

11. The computer program product of claim 8, wherein the neural network comprises a convolutional neural network.

12. The computer program product of claim 11, wherein the convolutional neural network comprises a U-net.

13. The computer program product of claim 8, wherein determining the probability that each pixel has an expected value based on the probability distributions comprises:

for each given pixel in the biomedical image having a given pixel value, identifying a probability value corresponding to the given pixel value in a given probability distribution corresponding to the given pixel.

14. The computer program product of claim 8, wherein detecting the anomaly in the biomedical image based on the plurality of expected pixel probabilities comprises:

comparing each expected pixel probability in the plurality of expected pixel probabilities to a predetermined threshold; and responsive to one or more of the plurality of expected pixel probabilities being less than the predetermined threshold, determining that the biomedical image has an anomaly.

15. An apparatus, comprising:

a processor; and a memory coupled to the processor, wherein the memory comprises instructions which, when executed by the processor, cause the processor to implement a knockout autoencoder engine for detecting anomalies in biomedical images, wherein the instructions cause the processor to:

train a neural network to be used as a knockout autoencoder that predicts an original image based on an input image, wherein training the neural network comprises:
        for each training image in a set of training images, selecting one or more knockout patches of the training image, filling the one or more knockout patches with noise to form a knockout image, and training the neural network to predict the training image based on expected content in the knockout patches of the knockout image given remaining pixels in the knockout image;

provide, by the knockout autoencoder engine, a biomedical image as the input image to the neural network;

output, by the neural network, a probability distribution for each pixel in the biomedical image, wherein each probability distribution represents a predicted probability distribution of expected pixel values for a given pixel in the biomedical image;

determine, by an anomaly detection component executing within the knockout autoencoder engine, a probability that each pixel has an expected value based on the probability distributions to form a plurality of expected pixel probabilities;

detect, by the anomaly detection component, an anomaly in the biomedical image based on the plurality of expected pixel probabilities;

mark, by an anomaly marking component executing within the knockout autoencoder engine, the detected anomaly in the biomedical image to form a marked biomedical image; and output, by the knockout autoencoder engine, the marked biomedical image.

16. The apparatus of claim 15, wherein determining the probability that each pixel has an expected value based on the probability distributions comprises:

for each given pixel in the biomedical image having a given pixel value, identifying a probability value corresponding to the given pixel value in a given probability distribution corresponding to the given pixel.

17. The apparatus of claim 15; wherein detecting the anomaly in the biomedical image based on the plurality of expected pixel probabilities comprises:

comparing each expected pixel probability in the plurality of expected pixel probabilities to a predetermined threshold; and responsive to one or more of the plurality of expected pixel probabilities being less than the predetermined threshold, determining that the biomedical image has an anomaly.

18. The apparatus of claim 15, wherein the set of training images comprise a plurality of biomedical images of healthy patients.

19. The apparatus of claim 15, wherein selecting one or more knockout patches comprises selecting one or more random patches in the training image.

20. The apparatus of claim 15, wherein the neural network comprises a convolutional neural network.

\* \* \* \* \*